(12) United States Patent
Bradicich et al.

(10) Patent No.: US 7,925,389 B2
(45) Date of Patent: Apr. 12, 2011

(54) METHOD OF DETECTING RECIRCULATION OF HEATED AIR WITHIN A RACK ENCLOSURE

(75) Inventors: Thomas Michael Bradicich, Apex, NC (US); Angela Beth Dalton, Durham, NC (US); Richard Edwin Harper, Chapel Hill, NC (US); William Joseph Piazza, Holly Springs, NC (US)

(73) Assignee: International Business Machines Corporation, Armonk, NY (US)

( * ) Notice: Subject to any disclaimer, the term of this patent is extended or adjusted under 35 U.S.C. 154(b) by 979 days.

(21) Appl. No.: 11/424,331

(22) Filed: Jun. 15, 2006

(65) Prior Publication Data

US 2007/0291817 A1 Dec. 20, 2007

(51) Int. Cl.
G05D 23/00 (2006.01)
G01K 13/00 (2006.01)

(52) U.S. Cl. .............. 700/299; 702/130; 703/7; 703/23; 374/100

(58) Field of Classification Search .......... 700/276–278, 700/299, 280–282; 702/130; 374/15, 100; 703/9, 13, 4, 6, 7, 21, 22
See application file for complete search history.

(56) References Cited

U.S. PATENT DOCUMENTS

| | | | |
|---|---|---|---|
| 4,164,172 A * | 8/1979 | Anderten et al. ............. 454/229 |
| 6,415,617 B1 * | 7/2002 | Seem ............................. 62/186 |
| 6,438,504 B2 | 8/2002 | Mikubo et al. | |
| 6,516,292 B2 | 2/2003 | Yahalom | |
| 6,522,954 B1 * | 2/2003 | Kummerer et al. ........... 700/278 |
| 6,574,104 B2 * | 6/2003 | Patel et al. .................... 361/695 |
| 6,694,759 B1 * | 2/2004 | Bash et al. ...................... 62/180 |
| 6,826,456 B1 * | 11/2004 | Irving et al. .................. 700/299 |
| 6,889,908 B2 | 5/2005 | Crippen et al. | |
| 6,922,787 B2 | 7/2005 | Karpel et al. | |
| 6,967,283 B2 * | 11/2005 | Rasmussen et al. ............ 174/50 |
| 7,262,962 B1 * | 8/2007 | McLeod et al. ............... 361/687 |
| 7,324,877 B2 * | 1/2008 | Tanaka et al. ................. 700/300 |
| 2003/0158718 A1 * | 8/2003 | Nakagawa et al. ............. 703/13 |
| 2004/0240514 A1 * | 12/2004 | Bash et al. .................... 374/109 |
| 2006/0036417 A1 * | 2/2006 | Wu et al. .......................... 703/9 |
| 2006/0047466 A1 * | 3/2006 | White ........................... 702/130 |
| 2007/0187343 A1 * | 8/2007 | Colucci et al. ................. 211/26 |

* cited by examiner

Primary Examiner — Kidest Bahta
Assistant Examiner — Sheela Rao
(74) Attorney, Agent, or Firm — Cynthia G. Seal; Jeffrey L. Streets

(57) ABSTRACT

A system and method of detecting recirculation within a rack server system. A heat transfer model is constructed for a rack server system. A recirculation zone is specified, and hypothetical recirculation temperatures are input at the recirculation zone. The heat transfer model predicts temperatures elsewhere in the rack severe system, and a predicted temperature profile is computed. Actual temperatures in the rack server system are sensed, and an actual temperature profile is also generated. The actual temperature profile is compared with the predicted temperature profile to detect potential recirculation.

19 Claims, 5 Drawing Sheets

METHOD OF DETECTING RECIRCULATION OF HEATED AIR WITHIN A RACK ENCLOSURE

BACKGROUND OF THE INVENTION

1. Field of the Invention

The present invention relates to methods and systems for modeling heat transfer within data processing systems.

2. Description of the Related Art

Large computer systems are often consolidated into centralized data centers, which can be less problematic and expensive than separately administering a multitude of scattered smaller servers. Rack systems, for example, conserve space and put the servers and infrastructure within easy reach of an administrator. For example, some of the more compact server arrangements currently available include blade servers. A blade server, such as the IBM eServer BLADECENTER (IBM and BLADECENTER are registered trademarks of International Business Machines Corporation, Armonk, N.Y.), is a type of rack-optimized server that eliminates many of the complications of previous generation rack servers. Blade server designs range from ultra-dense, low-voltage, lesser-performing severs to high performance, lower density servers to proprietary, customized solutions that include some blade features.

Due to the compact nature of rack systems, individual servers share a thermal profile with other hardware, such as enclosures, power supplies, fans and management hardware. Monitoring and managing power consumption and cooling is therefore critical. Because of the large number of elements typically housed within rack systems, the airflow and heating patterns are fairly complicated. Many possible sources of thermal problems can exist, exacerbating the detrimental effects of failures and complicating maintenance procedures.

U.S. Pat. No. 6,889,908 decribes a technique for diagnosing thermal anomalies in electronic equipment by introducing fault scenarios into a Flow Network Model of the equipment, and determining which fault predicts a set of expected temperatures that match observed temperatures. Some embodiments receive temperature readings associated with elements of a system. The temperature readings are dependent upon airflow and heating patterns of the elements. Differences between the temperature readings and expected temperatures are detected. Potential airflow and heating patterns associated with a thermal problem are then identified. Some embodiments, in particular, collect temperature readings from temperature sensors within an enclosure of the system and select a failure scenario associated with a root cause of thermal problem that is similar to the thermal problem described by the temperature readings collected.

Recirculation of heated air is another issue rack mounted equipment. Rack systems typically house a number of elements having interrelated airflow and heating patterns. Recirculation can be induced in open areas between the rack-mounted equipment, such as in and around empty slots. Ideally, these rack openings are blocked off by bolting blank filler panels to the rack frame. If the blank filler panels are left off, however, the pressure difference created by fans within the rack mounted equipment can force heated exhaust air to travel forward through the rack via a missing panel to the front of the equipment, where it is sucked back in. Another way heated air may recirculate is if the rack is placed near a wall, such that air vented from the back of the rack is deflected or channeled back towards the front.

Recirculation of warm air can cause rack mounted equipment to experience a substantial temperature increase. The additional heat introduced to the equipment by recirculating warm air may cause the equipment to exceed thermal thresholds, particularly if the equipment is operating in a room that is very warm to begin with, or if the amount of heating that takes place within the equipment is substantial. These high temperatures can cause the equipment to shut down or require it to be removed from services. Some portions of rack mounted equipment may experience more recirculation than others, which may interfere with the proper diagnosis of thermal problems. The difference between ambient room temperature air and heated air exiting from the back of rack mounted equipment can easily be 20 to 30° C. or more. If some of this exhaust air re-enters the equipment, it can cause the equipment to run warmer.

Therefore, there remains a need for an improved system and method for thermal analysis within a data processing system such as a rack enclosure. It would be desirable for the system nd method to more fully account for recirculation of air, thereby improving the reliability and effectiveness of operating the rack enclosure or other data processing system.

SUMMARY OF THE INVENTION

In one embodiment, a heat transfer model of an electronic system is created and used to detect recirculation of heated air into the system. The electronic system includes one or more heat generating elements. One or more recirculation zones are specified within the heat transfer model, and or more recirculation temperatures are selected, corresponding to the one or more recirculation zones. A first predicted temperature profile is computed for the electronic system using the heat transfer model and the one or more selected recirculation temperature profile is compared with the first predicted temperature profile, to detect potential recirculation of heated air.

In another embodiment, recirculation is detected within a rack enclosure. Temperature sensors within the rack enclosure are used to sense or measure actual temperatures. One or more recirculation zones are defined in a computer model of the rack enclosure so that the heat transfer within the rack enclosure can be modeled, including the effects of heated air recirculation at the one or more recirculation zones, to predict temperatures at locations within the rack enclosure. Locations of the predicted temperature are mapped to locations of the temperature sensors positioned within the rack enclosure. The predicted temperatures are compared with the actual temperatures to detect recirculation of heated air.

In yet another embodiment, a machine-accessible medium contains instructions which, when executed by a machine to perform operations, described herein.

DETAILED DESCRIPTION OF PREFERRED EMBODIMENTS

The present invention provides systems and methods for characterizing heating patterns within electronic systems, and, in particular, for detecting and analyzing the effects of recirculation of heated air. The invention may be used with a wide variety of electronic systems having heat generating components. Embodiments of the invention are particularly useful in conjunction with rack mounted server systems ("rack systems"), which may house a large number of components. Many of the components generate heat or otherwise affect heat transfer throughout the rack system. Thus, rack systems are discussed extensively below in that context. Discussions of rack systems, however, are not intended to limit the scope of the invention to applications involving rack systems.

A wide range of rack systems may benefit from the invention. For example, one rack system useful with the invention might include a single server mounted in a rack. Such a rack system would likely have many internal components such as CPUs, memory DIMMs, etc., and would typically be covered on the front by a grillwork to allow the entry of air for cooling purposes. Alternatively, a rack system might include components like CPUs, memory, etc., and the individual server blades might have grillwork or other openings to allow cooling air to enter. However, the blade chassis would not typically include grillwork at the front, as it would hinder the insertion and removal of server blades. The invention will be useful in many other rack systems that will be apparent to those skilled in the art.

Figure 1:
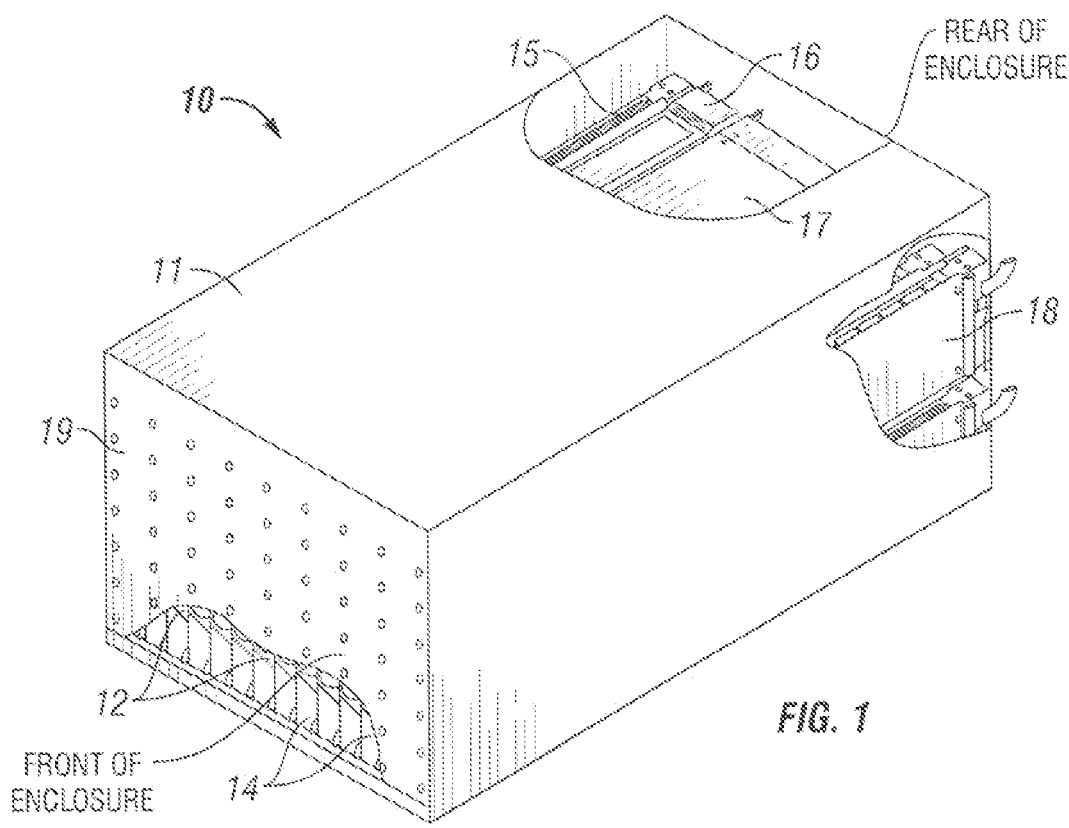
FIG. 1 is a partial cutaway perspective view of rack server system.

FIG. 1 is partial cutaway perspective view of a hypothetical rack system 10. Due to the wide range of rack systems that may benefit from the invention, the conceptually depicted rack system 10 is not intended to designate any particular make, model or variety. The hypothetical rack system 10 includes an enclosure 11 housing many components, such as servers 12, vents 14, a management controller module 15, a power module 16, a blower 17, and a switch module 18. The enclosure 11 includes an optional grillwork 19. The enclosure 11 may house multiple servers 12 sharing common management controllers, power modules, blowers, and switch modules. In many embodiments, connectors may couple the servers 12 with the support modules to reduce wiring requirements and facilitate installation and removal of the servers 12. For instance, each server 12 may couple with a gigabit Ethernet network via the switch module 18. The enclosure 11 may couple the server 12 to the Ethernet network without connecting cables directly to each server.

The enclosure 11 may also provide for hot-swappable components, allowing, for example, a server to be installed in an empty slot while other servers continue to function. In several embodiments, the enclosure 11 also includes one or more disc drivers, hard drives, compact disc (CD) drives, and digital versatile disc (DVD) drives to couple with the servers. The drives may facilitate installation of operating systems and other applications on the servers 12.

Servers 12 may include single or multi-processor servers having hard drives and memory to service one or more common or independent networks. In an embodiment shown, the servers 12 are hot-swappable blade servers. The servers 12 include vents 14 to facilitate forced air intake and exhaust to remove heat produced by components of the rack system 10. In particular, the blower 17 may draw air from the front of enclosure, through servers 12, and exhaust the air through the back of the blower 17 or the back of enclosure.

Temperature sensors may be positioned at locations throughout the enclosure 11. The temperature sensors may be coupled with the management controller 15 to monitor temperatures at the different locations throughout enclosure 11. The management controller 15 may include thermal analysis software, firmware and or state machines to analyze temperatures detected by describing the topology of the rack system 10. In particular, management controller 15 maintains the topology of the rack system 10 like the component content, interconnection of air paths between components, and attributes of each component, including for example, the airflow impedances of components such as servers 12, empty server slots, vents 14, management module 15, power module 16, blower 17, and switch module 18. The management controller 15 may further maintain topology with regard to the positions of the temperature sensors.

In some embodiments, the management controller 15 maintains an updated system topology by monitoring changes to components that affect the topology of the system and airflow and heating patterns. In other embodiments, a service provider, upon making such changes, may manually enter changes to the topology.

Still referring to FIG. 1, some aspects of heat transfer in the rack system 10, such as airflow impedances of individual components, may be modeled using methods such as Flow Network Modeling, to compute a single value that corresponds to the airflow impedance of the overall system. The intersection of the total system airflow impedance and the system level characteristic curve of all air-moving devices like the blower 17 may determine the pressure drop throughout the entire system. The airflow rate and pressure drops associated with the components may be determined from the pressure drop of the system and the individual impedances of the components.

Potential failures scenarios may also be taken into account when modeling heat transfer. Failure scenarios may include blockage of one or more vents, overheating of one or more processors in the remaining servers, removal of a ventilation cover for maintenance, and other events that can affect airflow and heating patterns in the rack system 10. These failure scenarios may also be updated in response to a change in the system topology. For instance, when one of the servers 12 is removed from the rack system 10 and the system topology is updated, failure scenarios related to the emptied server slot may be identified.

Figure 2:
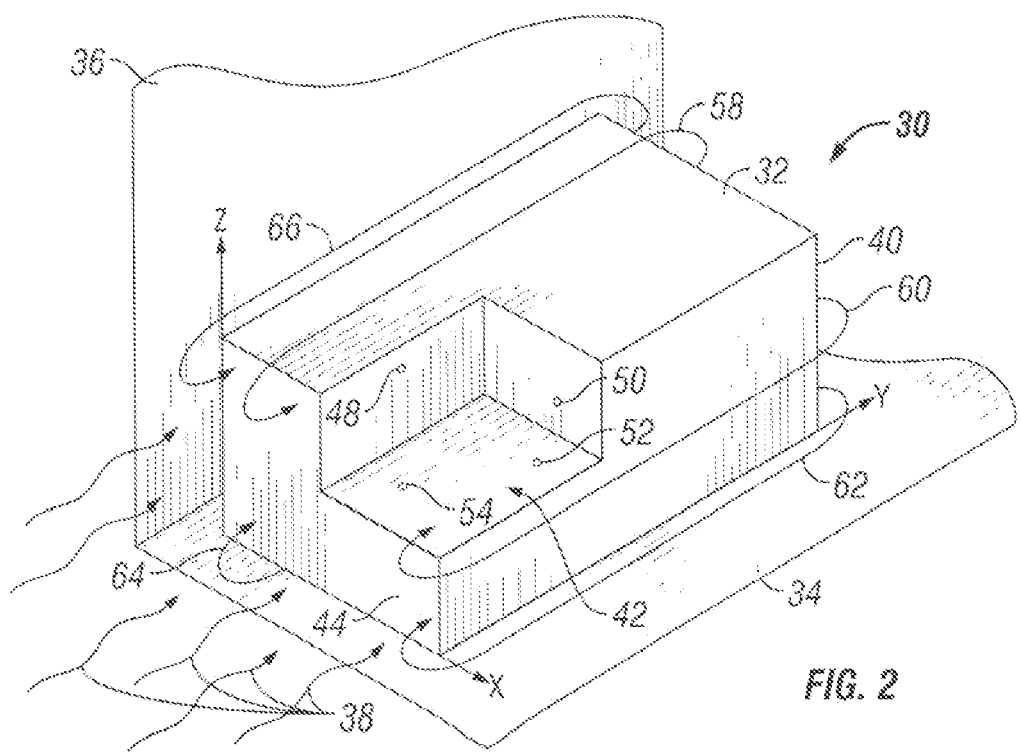
FIG. 2 is a partial cutaway perspective view of a rack server system illustrating airflow and recirculation within an enclosure.

When a thermal problem is detected, management controller 15 may analyze the temperature readings from the temperature sensors in enclosure 11 to determine the source, or root cause, of the thermal problem. Temperature and/or temperature gradients within the enclosure 11 are compared with the temperatures and/or temperature gradients of failure scenarios to determine the probable cause(s) of the thermal problem. The failure scenario(s) with the most similar temperatures and/or temperature gradients can be identified as the probable cause(s) of the thermal problem.

known techniques for modeling heat transfer have failed, however, to recognize, identify and account for the effects of recirculation of heated air in a rack system. Recirculation of heated air can significantly affect the heating patterns within a rack system. Thus, aspects of the invention are directed to detecting and analyzing recirculation of heated air. FIG. 2 is a conceptual cutaway view of a rack system 30 depicting airflow and recirculation within an enclosure 32. The enclosure 32 is supported on a floor 34 or in an equipment rack (not shown) adjacent to a wall 36. Ambient air enters the enclosure 32 from the front 44 in the direction of arrows 38, and exit the enclosure 32 at the rear 40. A cutaway of rack system 30 is generally indicated at 42, revealing a portion of the interior of rack system 30. Several temperature sensors 48, 50, 52, and 54 are located within the rack system 30. The locations of the temperature sensors 48, 50, 52, and 54 may be identified with respect to "x," "y," and "z" axes shown in FIG. 2.

Several potential recirculation pathways ("paths") 58, 60, 62, 64, and 66 are indicated, by way of example, around the enclosure 32. Recirculation may occur when air exiting the enclosure 32 from the rear 40 re-enters the enclosure 32 at the front 44. As illustrated, recirculation may occur where the rack system 30 is close to a wall, floor, or other boundary. The path 62 is in proximity to the floor 34. Path 66 is along the wall 36. Path 64 passes underneath the enclosure 32, near both the wall 36 and the floor 34. Recirculation may even occur, to some extent, at locations away from a floor, wall or other boundary. The path 60, for example, indicates air recirculating along the side of the enclosure 32 furthest from the wall 36.

Figure 3:
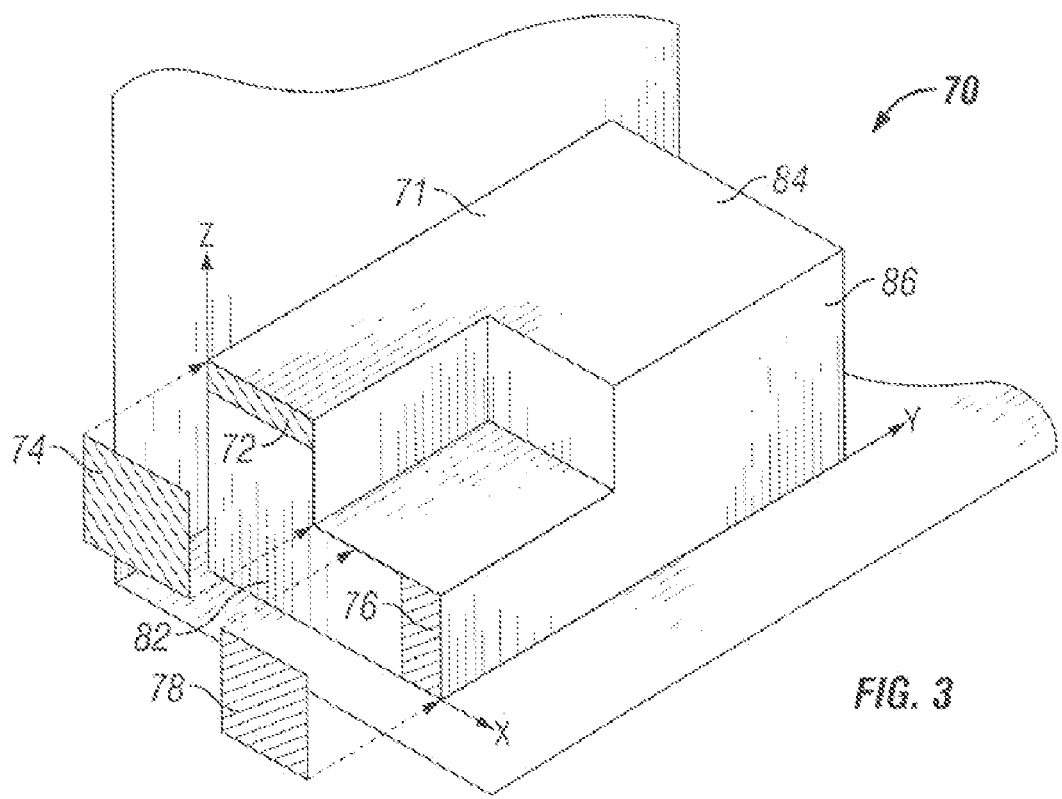
FIG. 3 is a partial cutaway perspective view of a rack server system illustrating examples of recirculation zones.

A "recirculation zone" may be defined as a zone or location where air has the potential to return to an upstream point in the normal air flow pathway of a rack system. FIG. 3 is a partial cutaway perspective view of a rack system 70 illustrating exemplary locations and configurations of some recirculation zones 72, 74, 76, and 78. Each of the recirculation zones 72, 74, 76, and 78 are hatched in FIG. 3 as a visual aid. The rack system 70 includes an enclosure 71 having a front face 82, an upper face 84, and a side face 86. The recirculation zone 72 is shown along the left upper front face 82, near an edge between the front face 82 and the upper face 84. The recirculation zone 72 is a generally planar boundary through which heated air can re-enter the enclosure 71. The recirculation zone 74 is also a generally planar boundary on the front face 82 through which heated air may re-enter the enclosure 71. As indicated by dashed lines, the recirculation zone 74 overlaps the recirculation zone 72 at an intersection equivalent to zone 72. In other words, zone 72 may be visualized as a subset of zone 74. According to some embodiments, overlapping zones 72 and 74 may be separately modeled to predict the effect of incrementally larger amounts of air recirculation. Although zones 72 and 74 run along the top left of the front face 82 to various distances down the front face 82, recirculation zones may be optionally defined anywhere on the front face 82. For example, zone 76 resides along the right side of the front face, at the intersection of front face 82 and side face 86. Zone 78 resides along the same intersection but covers a larger portion of the front face 82. Again, the zone 78 overlaps the zone 76, as indicated by dashed lines. Recirculation zones may also be optionally defined on a bottom, a side, a top, or possibly within an internal region of the rack system 70. However, the most preferred recirculation zones are along front edges, since a major amount of recirculating air would tend to enter the enclosure along these edges.

Figure 4:
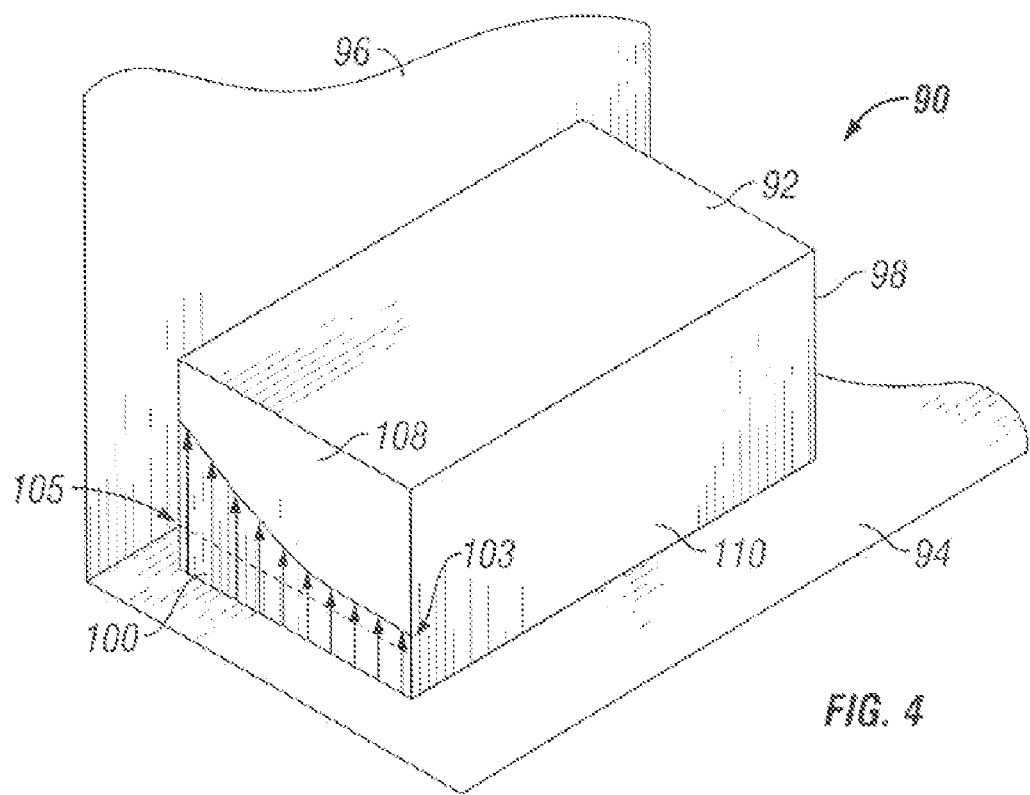
FIG. 4 is a perspective view of a rack server system illustrating a temperature gradient caused by recirculation of heated air.

In some embodiments, recirculation may result in temperature gradients across a recirculation zone. FIG. 4, for example, is a perspective view of a rack system 90 depicting various temperature gradients. An enclosure 92 is at least partially supported on a floor 94 or in an equipment rack, and is positioned adjacent to a wall 96. Air may recirculate from a rear 98 of the enclosure 92 to the front 108. A qualitative temperature distribution 100 is shown on the front 108 to indicate how recirculating air temperatures might be distributed. As shown, the observed temperature are higher on the left, in the vicinity of where the floor 94 and the wall 96 meet and provide more probable recirculation paths. Temperatures decrease toward a face 110 opposite wall 96, where there is more room around the enclosure 92 for air to dispute, rather than recirculate. A dashed line 105 represents room temperature as a reference. As shown, although temperatures within the temperature distribution 100 are generally greater than room temperature. This indicates that some amount of recirculation may occur away from the wall 96, and that even low levels of recirculation, such as at a location 103, can cause the temperature of air entering the enclosure 92 to rise.

Figure 5:
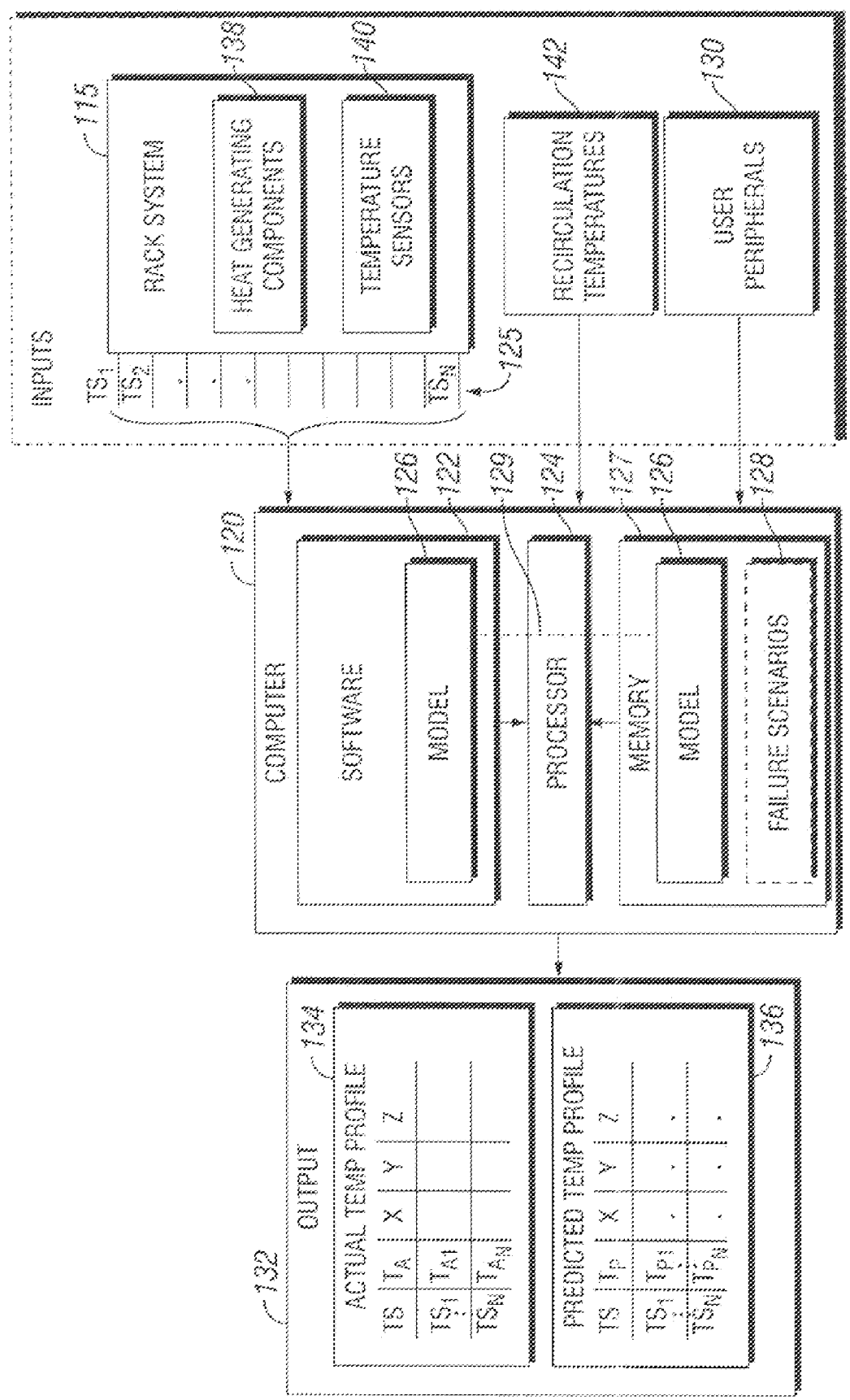
FIG. 5 is a schematic diagram of a system for detecting and analyzing recirculation in a rack system.

FIG. 5 is a schematic of a system for detecting and analyzing recirculation in a rack system 115. The rack system 115 houses heat generating components 138 and temperature sensors 140. A computer 120 includes software 122, a processor 124, and memory 126, and generates output 132. The computer 120 receives temperature readings and processes temperature signals 125 from the temperature sensors 140, to compute at least one "actual temperature profile" 134, included with the output 132. The actual temperature profile 134 is a data set that includes actual temperature (Ta) and position (x,y,z) information for each temperature sensor (TS). The actual temperature profile 134 may optionally be expresses visually as a chart, graph, listing of the data, or other visual representation. The actual temperature profile 134 may also be stored in the memory 127 for further processing by computer 120.

A heat transfer model 126 for rack system 115 is created by software 122 in the computer 120, and may be retained in the memory 127 as indicated by dashed line 129. The software 122 may include thermal analysis software and firmware for generating the model 126, for modeling heat transfer in the rack system 115. A user may input and define some aspects of the heat transfer model 126 via user peripherals 130, which may include a keyboard a pointing device, and an LCD display. The heat transfer model 126 may include heat transfer, airflow characteristics, and other parameters of the components 138.

One or more recirculation temperatures 142 are input to the model 120. The recirculation temperatures 142 are hypothetical, variable values selected for modeling at one or more recirculation zones of the rack system 115. The recirculation temperatures 142 may be selected by a user and input to the computer 120 using user peripherals 130. Alternatively, the computer 120 may generate recirculation temperatures to be modeled, such as through a process of iteration described below. Because recirculation relates to the re-entry of heated air, the recirculation temperatures are generally selected to be higher than a reference temperature, such as ambient air about the rack system 115, or an average room temperature where the rack system 115 is located. The recirculation temperatures may be stored in the memory 127 prior to running the model 126.

The computer 120 then runs the heat transfer model based on the input recirculation temperatures 142 and outputs a corresponding "predicted temperature profile" 136. The predicted temperature profile 136 is a data set that includes predicted temperature (Tp) and position (x,y,z) information corresponding to the locations of the temperature sensors 140. Thus, the predicted temperature profile 136 is a prediction of temperatures mapped to the locations of the temperature sensors 140, based on the model 126 and the recirculation temperatures 142 that were input to the model 126. The actual temperature profile(s) 134 may be compared with the predicted temperature profile(s) 136 to detect recirculation.

Figure 6:
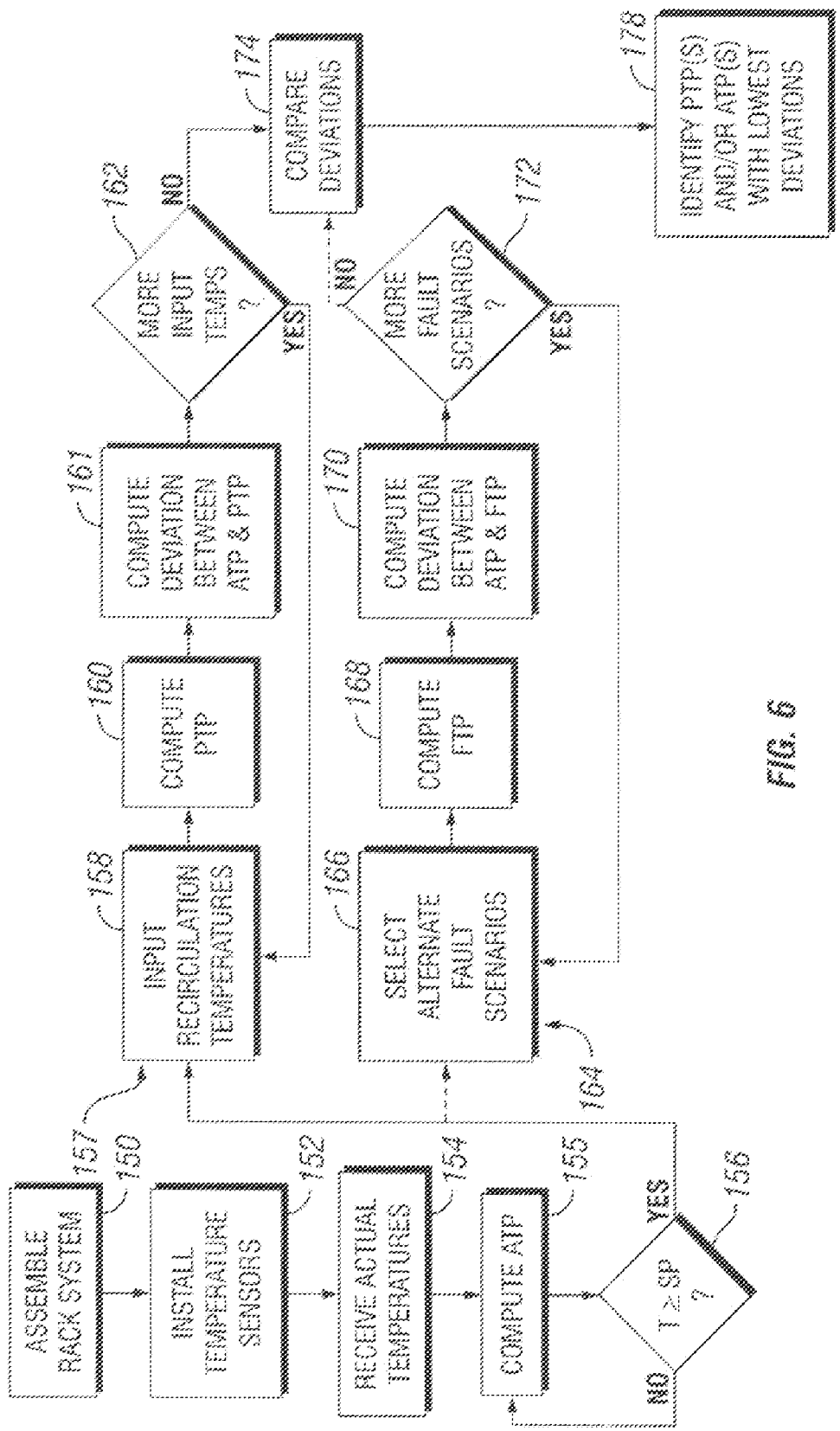
FIG. 6 is a flowchart describing a method of detecting recirculation within a rack system.

FIG. 6 is a flowchart describing a method of detecting recirculation within a rack system. A rack system is first assembled according to a system designer in step 150. Temperature sensors are positioned at locations throughout the rack system in step 152, and may be coupled with a computer. In general, the temperature sensors are at pre-assigned locations within the installed equipment but may be augmented by manually installed sensors as long as their location is provide as input to the compute, such as by entering the locations throughout the rack system in step 154 and computers an actual temperature profile (ATP) in step 155. The computer monitors the actual temperatures, and continuously checks to determine if an alarm condition has occurred. For example, the computer may monitor whether any of the actual temperatures being received exceed a certain set point (SP) in step 156.

If the set point or other alarm condition is activated in step 156, the computer begins computing one or more predicted temperature profiles (PTP) in PTP subroutine 157. Recirculation temperatures are input to the computer, and the computer runs the model to compute in predicted temperature profiles, where "n" is any positive integer. For example, in step 158 the first set of one or more recirculation temperatures is input to the computer. The computer runs the model and computes a deviation between the PTP and the ATP. As determined in step 162, the computer may optionally perform a process of iteration of the subroutine 157, varying temperatures or temperature distributions being modeled at the recirculation zones until, in step 162, the computer has computed a deviation between the ATP and the nth PTP. Known mathematical algorithms, such as least squares analysis, are available for computing the deviations. The user or system designer may select the best algorithm according to the rack system to be modeled. The number of iterations "n" may be fixed or identify the input temperature and/or more other input conditions that produce a PTP with minimum deviation from the ATP. Ultimately, it is not the primary goal of the invention to identify the theoretical temperature of a recirculation stream, but rather to identify that an undesireable level of recirculation is occurring.

In an optional FTP subroutine 164, the computer performs iterations wherein alternate fault scenarios are introduced, and wherein the effects of recirculation are excluded from the modeling process, to determine if the actual temperatures are more consistent with the alternate fault scenarios. In step 166 of the FTP subroutine 164, a fault scenario is selected to be modeled. In step 168, a fault-related temperature profile (x,y,z) information corresponding to the locations of the temperature sensors in the rack system. In step 170, the computer computes a deviation between FTP and the ATP. Step 172 determines how many iterations of FTP subroutine 164 will be performed based on the number of alternate fault scenarios to be modeled. In some embodiments, both recirculation and alternate fault scenarios may be modeled simultaneously. For example, the analysis may attempt to diagnose blocked intake vents in the presence of recirculating hot air.

In step 174, the computer compares the various deviations it has computed in PTP subroutine 157 and optional FTP subroutine 164. In some embodiments, the computer selects the PTP having the smallest deviation—in other words, the PTP that most closely compares to the ATP—and hence, the PTP that best describes actual temperatures within that none of the PTPs adequately describe the actual condition within the rack system. For example, if the deviations computed in step 168 of the FTP subroutine 164 are smaller than one or more of the alternate fault scenarios selected in step 166 more accurately describe the actual conditions within the rack system. Such determinations are made in step 178, such as by identifying the PTP(s) and/or ATP(s) having the lowest deviations.

If recirculation or one of the alternate fault scenarios is indicated in step 178, the computer may determine if a critical condition has been reached. For example, if the PTPs or FTPs describe a high probability of significant recirculation, or if actual temperatures being received are dangerously high, then the computer may activate a safety system. The safety system may include steps such as sounding an alarm, shutting down at least a portion of the rack system, and prompting the user to assess the recirculation problem. At this time, the computer may inform the user of relevant information, such as by displaying the actual temperature profile and any predicted temperature profiles that may describe the conditions in the rack system, as well as any alternate fault scenario that might indicate the source of a problem in the rack system.

Yet another beneficial use of the invention is to identify when a temperature sensor, such as a thermocouple, is giving an incorrect reading. If a particular temperature sensor is giving a temperature reading that is consistent with a particular scenario, such as a recirculation or failure scenario, but the model indicates that the temperature reading upstream and/or downstream in the normal air flow pattern are inconsistent with that particular temperature reading, then the model may indicate which temperature sensor may need maintenance or replacement.

It should be recognized that the invention may take the form of an entirely hardware embodiment, an entirely software embodiment, or an embodiment containing both hardware and software elements. In particular embodiments, including embodiments of methods, the invention may be implemented in software, which includes but is not limited to firmware, resident software and microcode.

Furthermore, the invention can take the form of a computer program product accessible from a computer-readable medium providing program code for use or in connection with a computer or any instruction execution system. For the purposes of this description, a computer-usable or computer readable medium can be any apparatus that can contain, store, communicate, propagate or transport the program for use by or in connection with the instruction execution system, apparatus or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provided temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public types network adaptors.

Figure 7:
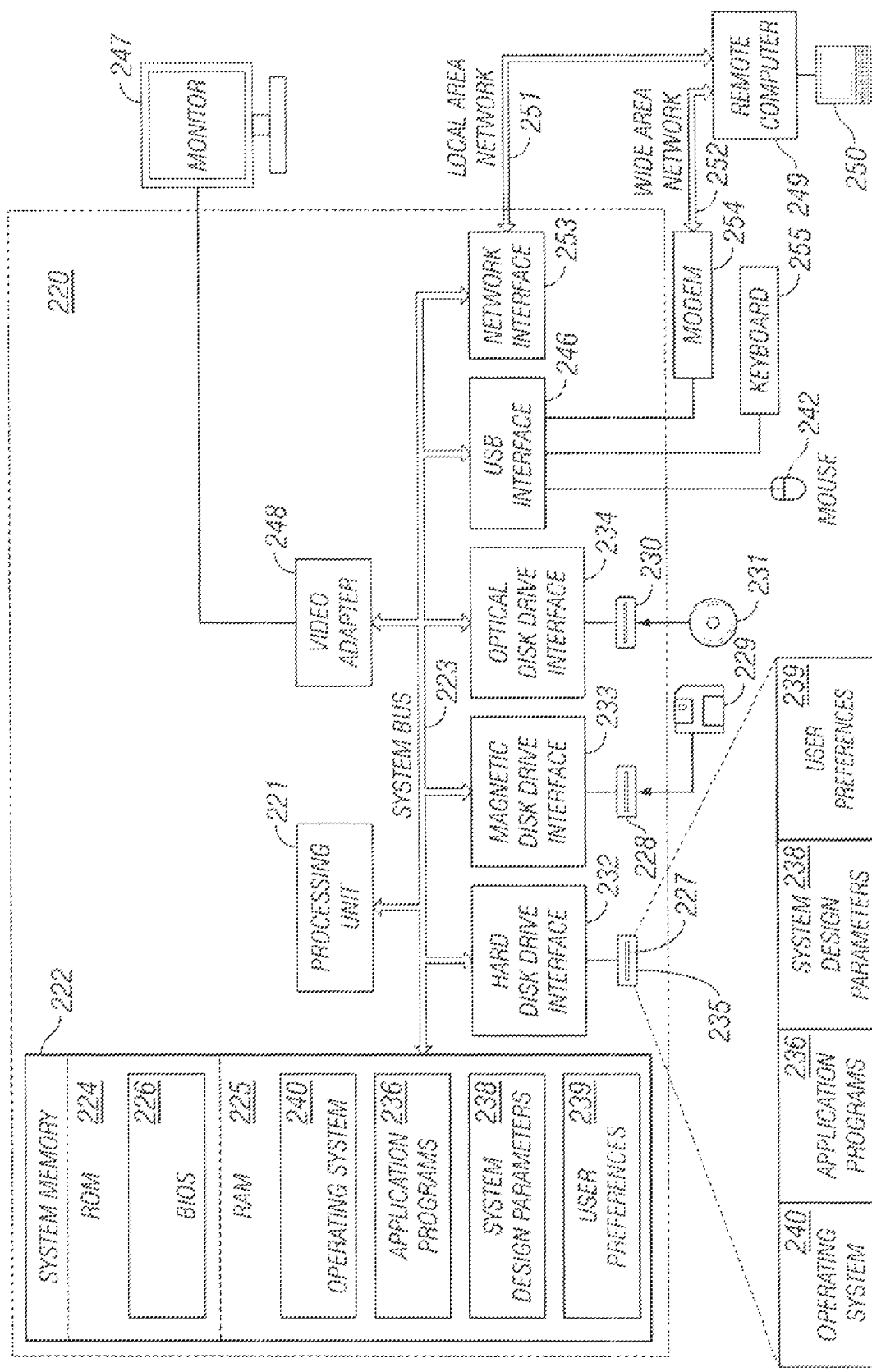
FIG. 7 is a schematic diagram of a computer system that may be configured for modeling heat transfer within a rack system.

To illustrate, FIG. 7 is a schematic diagram of a computer system 220 that may be configured for modeling heat transfer within a rack system according to an embodiment of the invention. The computer system 220 may be a general-purpose computing device in the form of a conventional computer system 220. Generally, computer system 220 includes a processing unit 221, a system memory 222, and a system bus 223 that couples various system components, including the system memory 222 to processing unit 221. System bus 223 may be any of several types of bus structures including a memory bus or memory controller, a peripheral bus, and a local bus using any of a variety of bus architectures. The system memory includes a read only memory (ROM) 224 and random access memory (RAM) 225. A basic input/ouput system (BIOS) 226, containing the basic routines that help to transfer information between elements within computer system 220, such as during start-up, is stored in ROM 224.

Computer system 220 further includes a hard disk 235 for reading from and writing to a hard disk 227, a magnetic disk drive 228 for reading from or writing to a removable magnetic disk 229, and an optical disk drive 230 for reading from or writing to a removable optical disk 231 such as a CD-R, CD-RW, DV-R, or DV-RW. Hard disk drive 235, magnetic disk drive 228, and optical disk drive 230 are connected to a system bus 223 by a hard disk drive interface 232, a magnetic disk drive interface 233, and an optical disk drive interface 234, respectively. Although the exemplary environment described herein employs hard disk 227, removable magnetic disk 229, and removable optical disk 231, it should be appreciated by those skilled in the art that other types of computer readable media which can store data that is accessible by a computer, such as magnetic cassettes, flash memory cards, digital video disks, Bernoulli cartridges, RAMs, ROMs, USB Drives, and the like, may also be used in the exemplary operating environment. The drives and their associated computer readable media provide nonvolatile storage of computer system 220. For example, the operating system 240 and application programs 236 may be stored in the RAM 225 and/or hard disk 227 of the computer system 220. Application programs 236 may include thermal analysis software and firmware for modeling heat transfer to detect and describe recirculation in the rack system.

A user may enter commands and information into computer system 220 through input devices, such as a keyboard 255 and a mouse 242. Other input devices (not shown) may include a microphone, joystick, game pad, touch pad, satellite dish, scanner, or the like. These and other input devices are often connected to processing unit 222 through a USB (universal serial bus) 246 that is coupled to the system bus 223, but may be connected by other interfaces, such as a serial port interface, a parallel port, game port, or the like. A display device 247 may also be connected to the system bus 223 via an interface, such as a video adaptor 248. In addition to the monitor, personal computers typically include other peripheral output devices (not shown), such as speakers and printers.

The computer system 220 may operate in a networked environment using logical connections to one or more remote computers 249. Remote computer 249 may be another personal computer, a server, a client, a router, a network PC, a peer device, a mainframe, a personal digital assistant, an internet-connected mobile telephone or other common network node While a remote computer 249 typically includes many or all of the elements described above relative to the computer system 249 typically includes many or all of the elements described above relative to the computer system 220, only a memory storage device 250 has been illustrated in FIG. 7. The logical connections depicted in the figure include a local area network (LAN) 251 and a wide area network (WAN) 252. Such networking environments are commonplace in offices, enterprise-wide computer networks, intranets, and the internet. Furthermore, temperature sensors distributed throughout the rack system to be modeled may be coupled to the computer system 220 via the LAN 251, WAN 252, or other logical connections.

When used in a LAN networking environment, the computer system 220 is often connected to the local area network 251 through a network interface or adaptor 253. When used in a WAN networking environment, the computer system 220 typically includes a modem 254 or other means for establishing high-speed communications over WAN 252, such as the internet. Modern 254, which may be internal or external, is connected to system bus 223 via USB interface 246. In a networked environment, program modules depicted relative to computer system 220, or portions thereof, may be stored in the remote memory storage device 250. It will be appreciated that the network connections shown are exemplary and other means of establishing a communications link between the computer may be used.

Program modules may be stored on hard disk 227, optical disk 231, ROM 224, RAM 225, or even magnetic disk 229. The program modules may include portions of an operating system 240 and application programs 236 for modeling heat transfer in the rack system. A system designer parameter database 238 may be included, which may contain parameters and procedures for modeling heat transfer in rack systems, as designated by a system designer. A user preference database 239 may also be included, which may contain parameters for modeling a specific rack system, as designed by an end user of the computer system 220. For example, a user may input information regarding rack system design, specific component locations, temperature sensor locations, recirculation temperatures and so forth.

Aspects of the present invention may be implemented in the form of application programs 236. The application program 236 generally comprises computer-executable instructions for modeling heat transfer within rack system. Application program 236 may be informed by or otherwise associated with system designer database 238 and/or user preferences database 239. For example, system designer database may include parameters involving components of the rack system, such as their locations and heat transfer characteristics. User preferences database 239 may also include information about components of the rack system, and may be updated by a user to account for changes in the configuration of the rack system.

The described example shown in FIG. 7 does not imply architectural limitations. For example, those skilled in the art will appreciate that methods of modeling heat transfer, detecting and evaluating recirculation, and so forth may be implemented in other computer system configurations, including rack system or blade server systems, multiprocessor systems, microprocessor based or programmable consumer electronics, network personal computers, minicomputers, mainframe computers, and the like. The invention may also be practiced in distributed computing environments, where tasks are performed by remote processing devices that are linked through a communications network. In a distributed computing environment, program modules may be located in both local and remote storage devices.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only to the attached claims.

What is claimed is:

1. A method, comprising:
   creating a heat transfer model of an electronic system, the electronic system including an enclosure having one or more heat generating elements;
   specifying a recirculation zone within the heat transfer model through which heated air can re-enter the enclosure;
   selecting one or more hypothetical temperature values for modeling at the recirculation zone;
   computing a first predicted temperature profile within the enclosure of the electronic system using the heat transfer model as a function of the one or more selected hypothetical temperature values at the recirculation zone, the first predicted temperature profile including predicted temperatures downstream of the recirculation zone;
   sensing an actual temperature profile within the enclosure of the electronic system, the actual temperature profile including actual temperatures downstream of the recirculation zone; and
   comparing the actual temperature profile with the first predicted temperature profile, to detect potential recirculation.

2. The method of claim 1, wherein the first predicted temperature profile includes position data corresponding to specified locations within the electronic system.

3. The method of claim 2, wherein the position data identifies locations of temperature sensors positioned within the electronic system, the temperature sensors for sensing the actual temperature profile.

4. The method of claim 1, further comprising:
   selecting other hypothetical temperature values corresponding to the recirculation zone;
   computing a second predicted temperature profile for the electronic system using the heat transfer model with the selected other hypothetical temperature values;
   comparing the actual temperature profile with the first and second predicted temperature profiles; and
   determining whether the first predicted temperature profile or the second predicted temperature profile more closely corresponds with the actual temperature profile.

5. The method of claim 4, further comprising:
   computing a first deviation between the first predicted temperature profile and the actual temperature profile;
   computing a second deviation between the second predicted temperature profile and the actual temperature profile; and
   comparing the first deviation with the second deviation.

6. The method of claim 4, wherein the other hypothetical temperature values are equal to an ambient air temperature.

7. The method of claim 1, wherein the one or more hypothetical temperature values are greater than an ambient air temperature.

8. The method of claim 1, wherein the recirculation zones includes a planar boundary on a front face of the enclosure of the electronic system.

9. The method of claim 1, wherein the recirculation zone is defined on one or more of a bottom, a side, and a top of the enclosure of the electronic system.

10. The method of claim 1, further comprising specifying a plurality of overlapping recirculation zones, and selecting the one or more hypothetical temperature values for modeling at the plurality of overlapping zones.

11. The method of claim 1, wherein the step of computing the first predicted temperature profile is performed concurrently with the step of sensing the actual temperature profile.

12. A method of detecting recirculation within a rack enclosure, comprising:
   providing temperature sensors within the rack enclosure;
   sensing actual temperatures using the temperature sensors;
   defining one or more recirculation zones within the rack enclosure;
   modeling heat transfer within the rack enclosure, including the effects of recirculation at the one or more recirculation zones, to predict temperatures at locations within the rack enclosure downstream of the one or more recirculation zones;
   modeling heat transfer within the rack enclosure, excluding the effects of recirculation at the one or more recirculation zones;
   mapping locations of the predicted temperatures to locations of the temperature sensors positioned within the rack enclosure; and
   determining whether the actual temperatures more closely correspond with the temperatures predicted when including the effects of recirculation or with the temperatures predicted when excluding the effects of recirculation.

13. The method of claim 12, wherein the one or more recirculation zones comprise a plurality of overlapping recirculation zones.

14. The method of claim 12, further comprising:
   selecting a plurality of different temperatures for modeling at the recirculation zone; and
   modeling heat transfer within the rack enclosure, including the effects of the plurality of different temperatures.

15. The method of claim 12, further comprising:
   modeling at least one temperature gradient across the one or more recirculation zones.

16. A computer program product including computer usable program code embodied on a computer usable medium for managing an air-cooled computer system, the computer program product including:
   computer usable program code for creating a heat transfer model of an electronic system, the electronic system including an enclosure having one or more heat generating elements;
   computer usable program code for specifying a recirculation zone within the heat transfer model through which heated air can re-enter the enclosure;
   computer usable program code for selecting one or more hypothetical temperature values for modeling at the recirculation zone;
   computer usable program code for computing a first predicted temperature profile within the enclosure of the electronic system using the heat transfer model as a function of the one or more selected hypothetical temperature values at the recirculation zone, the first predicted temperature profile including predicted temperatures downstream of the recirculation zone;

computer usable program code for sensing an actual temperature profile within the enclosure of the electronic system, the actual temperature profile including actual temperatures downstream of the recirculation zone; and computer usable program code for comparing the actual temperature profile with the first predicted temperature profile, to detect potential recirculation.

17. The computer program product of claim 16, further comprising:

computer usable program code for selecting other hypothetical temperature values corresponding to the recirculation zone;

computer usable program code for computing a second predicted temperature profile for the electronic system using the heat transfer model with the selected other hypothetical temperature values;

computer usable program code for comparing the actual temperature profile with the first and second predicted temperature profiles; and computer usable program code for determining whether the first predicted temperature profile or the second predicted temperature profile more closely corresponds with the actual temperature profile.

18. The computer program product of claim 16, further comprising:

computer usable program code for computing a first deviation between the first predicted temperature profile and the actual temperature profile;

computer usable program code for computing a second deviation between the second predicted temperature profile and the actual temperature profile; and computer usable program code for comparing the first deviation with the second deviation.

19. The computer program product of claim 16, wherein the first predicted temperature profile includes position data corresponding to specified locations within the electronic system, the position data identifying locations of temperature sensors positioned within the electronic system, the temperature sensors for sensing the actual temperature profile.

* * * * *